(12) United States Patent
Zhu et al.

(10) Patent No.: US 9,265,950 B2
(45) Date of Patent: *Feb. 23, 2016

(54) CONTRACTILITY MODULATION BASED ON IMPEDANCE SIGNAL

(75) Inventors: Qingsheng Zhu, Little Canada, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 936 days.

This patent is subject to a terminal disclaimer.

(21) Appl. No.: 12/152,099

(22) Filed: May 12, 2008

(65) Prior Publication Data

US 2008/0215108 A1    Sep. 4, 2008

Related U.S. Application Data

(63) Continuation of application No. 11/673,699, filed on Feb. 12, 2007, now abandoned, which is a continuation of application No. 10/411,795, filed on Apr. 11, 2003, now Pat. No. 7,177,681, which is a continuation of application No. 09/919,483, filed on Jul. 31, 2001, now Pat. No. 7,191,000.

(51) Int. Cl.
*A61N 1/00* (2006.01)
*A61N 1/362* (2006.01)
*A61N 1/365* (2006.01)
*A61N 1/368* (2006.01)

(52) U.S. Cl.
CPC .............. *A61N 1/3627* (2013.01); *A61N 1/3684* (2013.01); *A61N 1/36521* (2013.01)

(58) Field of Classification Search
CPC ........... A61N 1/36514; A61N 1/36521; A61N 1/3684; A61N 1/3627; A61N 1/3628
USPC ........................................ 600/547; 607/4–28
See application file for complete search history.

(56) References Cited

U.S. PATENT DOCUMENTS

| | | |
|---|---|---|
| 3,340,867 A | 9/1967 | Kubicek et al. |
| 3,871,359 A | 3/1975 | Pacela |
| 4,003,379 A | 1/1977 | Ellinwood |
| 4,059,169 A | 11/1977 | Hagen |
| RE30,101 E | 9/1979 | Kubicek et al. |
| 4,271,192 A | 6/1981 | Wurtman et al. |
| 4,437,469 A | 3/1984 | Djordjevich et al. |
| 4,450,527 A | 5/1984 | Sramek |
| 4,470,987 A | 9/1984 | Wurtman et al. |
| 4,472,420 A | 9/1984 | Toth |

(Continued)

FOREIGN PATENT DOCUMENTS

| | | |
|---|---|---|
| EP | 348271 | 12/1989 |
| EP | 0584388 | 3/1994 |

(Continued)

OTHER PUBLICATIONS

Notice of Allowance Dated Feb. 6, 2003 From the US Patent and Trademark Office Re.: U.S. Appl. No. 09/919,483.

(Continued)

*Primary Examiner* — Scott Getzow

(57) ABSTRACT

A cardiac rhythm management system detects edema. In response to an episode of detected edema, it initiates or adjusts a cardiac resynchronization therapy and/or a cardiac contractility modulation (CCM) therapy.

26 Claims, 8 Drawing Sheets

(56) References Cited

U.S. PATENT DOCUMENTS

| | | |
|---|---|---|
| 4,472,431 A | 9/1984 | Toth |
| 4,559,946 A | 12/1985 | Mower |
| 4,562,843 A | 1/1986 | Djordjevich et al. |
| 4,567,892 A | 2/1986 | Plicchi et al. |
| 4,576,183 A | 3/1986 | Plicchi et al. |
| 4,651,716 A | 3/1987 | Forester et al. |
| 4,693,253 A | 9/1987 | Adams |
| 4,880,005 A | 11/1989 | Pless et al. |
| 4,884,576 A | 12/1989 | Alt |
| 4,904,472 A | 2/1990 | Belardinelli et al. |
| 4,919,136 A | 4/1990 | Alt |
| 4,928,688 A * | 5/1990 | Mower ............ 607/9 |
| 4,980,379 A | 12/1990 | Belardinelli et al. |
| 4,987,897 A | 1/1991 | Funke |
| 5,002,052 A | 3/1991 | Haluska |
| 5,003,976 A | 4/1991 | Alt |
| 5,025,786 A | 6/1991 | Siegel |
| 5,031,629 A | 7/1991 | Demarzo |
| 5,113,869 A | 5/1992 | Nappholz et al. |
| 5,117,825 A | 6/1992 | Grevious |
| 5,178,154 A | 1/1993 | Ackmann et al. |
| 5,179,947 A | 1/1993 | Meyerson et al. |
| 5,199,428 A | 4/1993 | Obel et al. |
| 5,213,098 A | 5/1993 | Bennett et al. |
| 5,215,083 A | 6/1993 | Drane et al. |
| 5,233,985 A | 8/1993 | Hudrlik |
| 5,246,008 A | 9/1993 | Mueller et al. |
| 5,271,395 A | 12/1993 | Wahlstrand et al. |
| 5,273,034 A | 12/1993 | Nilsson |
| 5,282,836 A | 2/1994 | Kreyenhagen et al. |
| 5,282,840 A | 2/1994 | Hudrlik et al. |
| 5,284,136 A | 2/1994 | Hauck et al. |
| 5,292,343 A | 3/1994 | Blanchette et al. |
| 5,300,093 A | 4/1994 | Koestner et al. |
| 5,309,917 A | 5/1994 | Wang et al. |
| 5,313,953 A | 5/1994 | Yomtov et al. |
| 5,324,309 A | 6/1994 | Kallok |
| 5,324,315 A | 6/1994 | Grevious |
| 5,344,429 A | 9/1994 | Smits |
| 5,354,317 A | 10/1994 | Alt |
| 5,354,319 A | 10/1994 | Wyborny et al. |
| 5,355,894 A | 10/1994 | Sivard |
| 5,366,485 A | 11/1994 | Kroll et al. |
| 5,370,665 A | 12/1994 | Hudrlik |
| 5,404,877 A | 4/1995 | Nolan et al. |
| 5,405,362 A | 4/1995 | Kramer et al. |
| 5,411,031 A | 5/1995 | Yomtov |
| 5,431,682 A | 7/1995 | Hedberg |
| 5,441,525 A | 8/1995 | Shelton et al. |
| 5,443,073 A | 8/1995 | Wang et al. |
| 5,454,377 A | 10/1995 | Dzwonczyk et al. |
| 5,464,434 A | 11/1995 | Alt |
| 5,479,369 A | 12/1995 | Matsumura et al. |
| 5,501,701 A | 3/1996 | Markowitz et al. |
| 5,505,209 A | 4/1996 | Reining |
| 5,507,785 A | 4/1996 | Deno |
| 5,522,860 A | 6/1996 | Molin et al. |
| 5,526,808 A | 6/1996 | Kaminsky |
| 5,534,018 A | 7/1996 | Wahlstrand et al. |
| 5,540,728 A | 7/1996 | Shelton et al. |
| 5,562,711 A | 10/1996 | Yerich et al. |
| 5,562,712 A | 10/1996 | Steinhaus et al. |
| 5,626,623 A | 5/1997 | Kieval et al. |
| 5,642,734 A | 7/1997 | Ruben et al. |
| 5,676,686 A | 10/1997 | Jensen et al. |
| 5,685,316 A | 11/1997 | Schookin et al. |
| 5,706,829 A | 1/1998 | Kadri |
| 5,722,999 A | 3/1998 | Snell |
| 5,725,561 A | 3/1998 | Stroebel et al. |
| 5,725,562 A | 3/1998 | Sheldon |
| 5,732,710 A | 3/1998 | Rabinovich et al. |
| 5,749,369 A | 5/1998 | Rabinovich et al. |
| 5,749,900 A | 5/1998 | Schroeppel et al. |
| 5,782,774 A | 7/1998 | Shmulewitz |
| 5,782,879 A | 7/1998 | Rosborough et al. |
| 5,782,884 A | 7/1998 | Stotts et al. |
| 5,788,643 A | 8/1998 | Feldman |
| 5,791,349 A | 8/1998 | Shmulewitz |
| 5,800,464 A | 9/1998 | Kieval |
| 5,865,760 A | 2/1999 | Lidman et al. |
| 5,874,420 A | 2/1999 | Pelleg |
| 5,876,353 A | 3/1999 | Riff |
| 5,913,879 A | 6/1999 | Ferek et al. |
| 5,919,210 A | 7/1999 | Lurie et al. |
| 5,957,861 A * | 9/1999 | Combs et al. ............ 600/547 |
| 5,957,957 A | 9/1999 | Sheldon |
| 5,978,705 A | 11/1999 | Kenknight et al. |
| 6,026,324 A | 2/2000 | Carlson |
| 6,035,233 A | 3/2000 | Schroeppel et al. |
| 6,044,297 A | 3/2000 | Sheldon et al. |
| 6,049,735 A | 4/2000 | Hartley et al. |
| 6,075,015 A | 6/2000 | Sestelo et al. |
| 6,076,015 A * | 6/2000 | Hartley et al. ............ 607/20 |
| 6,078,834 A | 6/2000 | Lurie et al. |
| 6,095,987 A | 8/2000 | Shmulewitz et al. |
| 6,104,949 A | 8/2000 | Pitts et al. |
| 6,154,672 A | 11/2000 | Pendekanti et al. |
| 6,161,038 A | 12/2000 | Schookin et al. |
| 6,186,955 B1 | 2/2001 | Baura |
| 6,228,033 B1 | 5/2001 | Kobi et al. |
| 6,292,689 B1 | 9/2001 | Wallace et al. |
| 6,298,267 B1 | 10/2001 | Roborough et al. |
| 6,317,631 B1 | 11/2001 | Ben-Haim et al. |
| 6,336,903 B1 | 1/2002 | Bardy |
| 6,411,844 B1 | 6/2002 | Kroll et al. |
| 6,438,408 B1 | 8/2002 | Mulligan et al. |
| 6,463,324 B1 * | 10/2002 | Ben-Haim et al. ............ 607/9 |
| 6,473,640 B1 | 10/2002 | Erlebacher |
| 6,511,438 B2 | 1/2003 | Bernstein et al. |
| 6,512,949 B1 | 1/2003 | Combs et al. |
| 6,560,481 B1 | 5/2003 | Heethaar et al. |
| 6,561,986 B2 | 5/2003 | Baura et al. |
| 6,595,927 B2 | 7/2003 | Pitts et al. |
| 6,600,949 B1 | 7/2003 | Turcott |
| 6,602,201 B1 | 8/2003 | Hepp et al. |
| 6,625,492 B2 | 9/2003 | Florio et al. |
| 6,636,754 B1 | 10/2003 | Baura et al. |
| 6,643,543 B2 | 11/2003 | Takehara et al. |
| 6,714,813 B2 | 3/2004 | Ishigooka et al. |
| 6,738,667 B2 | 5/2004 | Deno et al. |
| 6,748,271 B2 | 6/2004 | Spinelli et al. |
| 6,752,765 B1 | 6/2004 | Jensen et al. |
| 6,811,537 B2 | 11/2004 | Bardy |
| 6,829,503 B2 | 12/2004 | Alt |
| 6,907,288 B2 | 6/2005 | Daum |
| 6,908,437 B2 | 6/2005 | Bardy |
| 6,912,420 B2 | 6/2005 | Scheiner et al. |
| 6,963,777 B2 | 11/2005 | Lincoln et al. |
| 7,096,064 B2 | 8/2006 | Deno et al. |
| 7,127,289 B2 | 10/2006 | Yu et al. |
| 7,127,290 B2 | 10/2006 | Girouard et al. |
| 7,130,678 B2 | 10/2006 | Ritscher et al. |
| 7,149,573 B2 | 12/2006 | Wang |
| 7,177,681 B2 | 2/2007 | Zhu et al. |
| 7,186,220 B2 | 3/2007 | Stahmann et al. |
| 7,191,000 B2 | 3/2007 | Zhu et al. |
| 7,226,422 B2 | 6/2007 | Hatlestsad et al. |
| 7,313,434 B2 | 12/2007 | Blealcazar et al. |
| 7,315,076 B2 | 1/2008 | Nomura et al. |
| 7,387,610 B2 | 6/2008 | Stahmann et al. |
| 2001/0020138 A1 | 9/2001 | Ishigooka et al. |
| 2002/0032467 A1* | 3/2002 | Shemer et al. ............ 607/2 |
| 2002/0115939 A1 | 8/2002 | Mulligan et al. |
| 2002/0123674 A1 | 9/2002 | Plicchi et al. |
| 2002/0138014 A1 | 9/2002 | Baura et al. |
| 2002/0147475 A1 | 10/2002 | Scheiner et al. |
| 2002/0147476 A1 | 10/2002 | Daum |
| 2002/0193689 A1 | 12/2002 | Bernstein et al. |
| 2003/0028221 A1 | 2/2003 | Zhu et al. |
| 2003/0055461 A1 | 3/2003 | Girouard et al. |
| 2003/0074029 A1 | 4/2003 | Deno et al. |
| 2003/0105496 A1 | 6/2003 | Yu et al. |
| 2003/0176896 A1 | 9/2003 | Lincoln et al. |
| 2003/0191503 A1 | 10/2003 | Zhu et al. |

(56) References Cited

U.S. PATENT DOCUMENTS

| | | |
|---|---|---|
| 2003/0220580 A1 | 11/2003 | Alt |
| 2004/0049235 A1 | 3/2004 | Deno et al. |
| 2004/0073128 A1 | 4/2004 | Hatlestad et al. |
| 2004/0102712 A1 | 5/2004 | Belalcazar et al. |
| 2004/0116819 A1 | 6/2004 | Alt |
| 2004/0133079 A1 | 7/2004 | Mazar et al. |
| 2004/0147982 A1 | 7/2004 | Bardy |
| 2004/0172080 A1 | 9/2004 | Stadler et al. |
| 2004/0215097 A1 | 10/2004 | Wang |
| 2004/0215270 A1 | 10/2004 | Ritscher et al. |
| 2005/0004609 A1 | 1/2005 | Stahmann et al. |
| 2005/0021098 A1 | 1/2005 | Spinelli et al. |
| 2005/0080460 A1 | 4/2005 | Wang et al. |
| 2005/0137480 A1 | 6/2005 | Alt et al. |
| 2005/0283197 A1 | 12/2005 | Daum et al. |
| 2006/0041280 A1 | 2/2006 | Stahmann et al. |
| 2006/0293609 A1 | 12/2006 | Stahmann et al. |

FOREIGN PATENT DOCUMENTS

| | | |
|---|---|---|
| EP | 0620420 | 10/1994 |
| EP | 0663219 | 7/1995 |
| EP | 1057498 | 12/2000 |
| EP | 1078597 | 2/2001 |
| EP | 606301 | 12/2001 |
| EP | 1247487 | 10/2002 |
| EP | 1275342 | 1/2003 |
| EP | 771172 | 4/2003 |
| WO | WO 84/00227 | 1/1984 |
| WO | WO8400227 | 1/1984 |
| WO | WO 93/04627 | 3/1993 |
| WO | WO9304627 | 3/1993 |
| WO | WO 96/01586 | 1/1996 |
| WO | WO9601586 | 1/1996 |
| WO | WO 97/37591 | 10/1997 |
| WO | WO 97/38628 | 10/1997 |
| WO | WO9737591 | 10/1997 |
| WO | WO9738628 | 10/1997 |
| WO | WO 98/51211 | 11/1998 |
| WO | WO9851211 | 11/1998 |
| WO | WO 01/41638 | 6/2001 |
| WO | WO0141638 | 6/2001 |
| WO | WO 02/053026 | 7/2002 |
| WO | WO 02/053228 | 7/2002 |
| WO | WO02053026 | 7/2002 |
| WO | WO02053228 | 7/2002 |
| WO | WO 03/020364 | 3/2003 |
| WO | WO03020364 | 3/2003 |

OTHER PUBLICATIONS

Notice of Allowance Dated Sep. 21, 2006 From the US Patent and Trademark Office Re.: U.S. Appl. No. 09/919,483.
Notice of Allowance Dated Mar. 22, 2005 From the US Patent and Trademark Office Re.: U.S. Appl. No. 09/919,483.
Notice of Allowance Dated Feb. 24, 2006 From the US Patent and Trademark Office Re.: U.S. Appl. No. 09/919,483.
Notice of Allowance Dated Sep. 29, 2006 From the US Patent and Trademark Office Re.: U.S. Appl. No. 10/411,795.
Official Action Dated Nov. 1, 2005 From the US Patent and Trademark Office Re.: U.S. Appl. No. 10/411,795.
Official Action Dated Oct. 4, 2004 From the US Patent and Trademark Office Re.: U.S. Appl. No. 09/919,483.
Official Action Dated Apr. 14, 2006 From the US Patent and Trademark Office Re.: U.S. Appl. No. 10/411,795.
Official Action Dated Aug. 22, 2002 From the US Patent and Trademark Office Re.: U.S. Appl. No. 09/010,483.
Response Dated Jul. 11, 2006 to Official Action of Apr. 14, 2006 From the US Patent and Trademark Office Re.: U.S. Appl. No. 10/411,795.
Response Dated Jan. 13, 2006 to Official Action of Nov. 1, 2006 From the US Patent and Trademark Office Re.: U.S. Appl. No. 10/411,795.
Supplemental Notice of Allowability Dated Apr. 14, 2006 From the US Patent and Trademark Office Re.: U.S. Appl. No. 09/919,483.
??? "Medtronic Announces European Release of Innovative Insync Sentry Cardiac Resynchronization Therapy defibrillator", http://www.medtronic.com/newsroom/news, 2004.
??? "Medtronic: Insync Sentry 7298: Dual Chamber Implantable Cardioverter Defibrillator With Cardiac Resynchronization Therapy (VVE-DDR) and Opti-Vol Fluid Monitoring: Reference Manual", www.medtronic.com.
Adamicza et al. "Changes in Transthoracic Electrical Impedance During Endotoxemia in Dogs", Acta Physiol Hung, 85(4):291-302, 1997. Abstract.
Adamicza et al. "Investigation of the Thoracic Electrical Impedance During Endotoxemia in Dogs", Acta chirurgica Hungarica, 36(1-4):1-3, 1997.
Baarends et al. "Body-Water Compartments Measured by Bio-Electrical Impedance Spectroscopy in Patients With Chronic Obstructive Pulmonary Disease", Clinical Nutrition, 17(1):15-22, Feb. 1998.
Belalcazar et al. "Improved Lung Edema Monitoring With Coronary Vein Pacing Leads", Pacing and Clinical Electrophysiology, 26(4 pt. II):933, Apr. 2003.
Belalcazar et al. "Improved Lung Edema Monitoring With Coronary Vein Pacing Leads: A Simulation Study", Physiological Measurement, 25: 475-487, 2004. Abstract.
Berman et al. "Transthoracic Electrical Impedance S A Guide to Intravascular Overload", Archive of Surgery, 102(1): 61-64, Jan. 1971.
Bradbury et al. "Assessment of the Sensitivity of Bioimpedance to Volume Changes in Body Water", Pediatr Nephrol, 9(3):337-340, Jun. 1995. Abstract.
Campbell et al. "Clinical Applications of Electrical Impedance Tomography in the Monitoring of Changes in Intrathoracic Fluid Volumes", Physiol Meas., 15: 217-222, 1994.
Campbell et al. "Detection of Changes in Intrathoracic Fluid in Man Using Electrical Impedance Tomography", Clinical Science, 87: 97-101, 1994. Abstract.
Charach et al. "Transthoracic Monitoring of the Impedance of the Right Lung in Patients With Cardiogenic Pulmonary Edema" Crit Care Medicine, 29(6): 1137-1144, Jun. 2001. Abstract.
Chiolero et al. "Assessment of Changes in Body Water by Bioimpedance in Acutely Ill Surgical Patients", Intensive Care Medicine, 18(6):322-326, 1992. Abstract.
Daum et al. "Systems and Methods for Hypotension", U.S. Appl. No. 11/141,260, filed May 31, 2005, 51 Pages. Abstract.
Defaye et al. "Automatic Recognition of Abnormal Respiratory Events During Sleep by a Pacemaker Transthoracic Impedance Sensor", Journal of Cardiovascular Electrophysiology, 15(9):1034-1040, Sep. 2004.
Denniston et al. "Factors Influencing the Measurement of Stroke Volume by Electrical Impedance", Physiology (1372-1377), Cardiac Output, Abstract No. 1373, 463.
Denniston et al. "Measurement of Pleural Effusion by Electrical Impedance", Journal of Applied Physiology, 38(5): 851-857, May 1975. Abstract.
Ebert et al. "The Use of Thoracic Impedance for Determining Thoracic Blood Volume Changes in Man", Aviat Space Environ Med., 57(1): 49-53, Jan. 1986.
Eckhard et al. "Control of Pacemaker Rale by Impedance-Based Respiratory Minute Ventilation", Chest, 92(2): 247-252, Aug. 1987.
Ellenbogen et al. "Rate-Adaptive Pacing Based on Impedance-Derived Minute Ventilation", Clinical Cardiac Pacing, Philadelphia Saunders, p. 219-233, 1995.
Ellenbogen et al. "The Electrode-Tissue Interface and the Foreign Body Response", Clinical Cardiac Pacing, Excerpt, p. 22-23, 1995.
Fein et al. "Evaluation of Transthoracic Electrical Impedance in the Diagnosis of Pulmonary Edema", Circulation, 60(5): 1156-1160, Nov. 1979.
Foreman et al. "Intra-Thoracic Impedance: A Surrogate Measure of Thoracic Fluid—Fluid Accumulation Status Trial (Fast)", Journal of Cardiac Failure, 10(4 Suppl), 2004.
Frerichs et al. "Electrical Impedance Tomography in Monitoring Experimental Lung Injury", Intensive Care Med., 24(8):829-836, Aug. 1998. Abstract.

(56) References Cited

OTHER PUBLICATIONS

Garland et al. "Measurement of Extravascular Lung Water in Hemodialysis Patients Using Blood Ultrasound Velocity and Optical Density Dilution", ASAIO Journal, 48(4):398-403, Jul.-Aug. 2002. Abstract.
Goovaerts et al. "Microprocessor-Based System for Measurement of Electrical Impedances During Haemodialysis and in Postoperative Care", Medical & Biological Engineering & Computing, 26: 75-80, Jan. 1988. Abstract.
Gotshall et al. "Bioelectric Impedance as an Index of Thoracic Fluid", Aviation Space and Environmental Medicine, 70(1):58-61, Jan. 1999. Abstract.
Grimbert et al. "Pulmonary Water and Thoracic Impedance Evaluation of a Measurement Technic", Annales de l'anesthésiologie française, 16 Spec (2-3):157-163, 1975. Abstract.
Harris et al. "Applications of Applied Potential Tomography (APT) in Respiratory Medicine", Clinical physics and physiological measurement, 8 Suppl A: 155-165, 1987. Abstract.
Hoon et al. "Changes in Transthoracic Electrical Impedance at High Altitude", British Heart Journal, 39(1): 61-66, 1977.
Hull et al. "The Transthoracic Impedance Method for the Determination of the Degree and Change in Extravascular Water", Acta. Tubere. Pneumol. Belg., 68(4): 369-377, 1977.
Hull et al. "Transthoracic Electrical Impedance: Artifacts Associated With Electrode Movement", Resuscitation, 6(2): 115-124, 1978.
Ishibe et al. "Transthoracic Electrical Impedance Method for Measurement of Pulmonary Edema in Vivo", Masul, 27(13):1559-1567, Dec. 1978.
Joekes et al. "Impedance Cardiography—Its Value in an Intensive Care Unit", Materiels Et Techniques/Cardiocirculatory Equipment and Technics, Abstract No. 141, 1 Page.
Keller et al. "Monitoring of Pulmonary Fluid Volume and Stroke Volume by Impedance Cardiography in Patients on Hemodialysis,", Chest, 72(1): 56-62, Jul. 1977.
Khan et al. "Quantitative Electrical-Impedance Plethysmography for Pulmonary Oedema", Medical & Biological Engineering & Computing, 15: 627-633, Nov. 1977. Abstract.
Kiesler et al. "Impedance Cardiography by Use of a Spot-Electrode Array to Track Changes in Cardiac Output in Anesthetized Dogs", Journal of the American Veterinary Medical Association, 196(11): 1804-1810, Jun. 1990. Abstract.
Koizumi "Changes of Transthoracic Impedance (Zinf 0 and Deltaz) in Newborn Infants", Acta Neonatol. Jpn., 14(3):335-340, 1978.
Kunst et al. "Electrical Impedance Tomography in the Assessment of Extravascular Lung Water in Noncardiogenic Acute Respiratory Failure", Chest, 116(6): 1695-1702, Dec. 1999.
Kusumoto et al. "Medical Progress: Cardiac Pacing", New England Journal of Medicine, 334(2): 89-98, Jan. 1996. Abstract.
Larsen et al. "Influence of Furosemide and Body Posture on Transthoracic Electrical Impedance in AMT, Chest, 90(5):733-737, Nov. 1986.
Lau "The Range of Sensors and Algorithms Used in Rate Adaptive Cardiac Pacing", Pace, 15(8):1177-1211, Aug. 1992. Abstract.
Lau et al. "Rate-Responsive Pacing With a Pacemaker That Detects Respiratory Rate (Biorate): Clinical Advantages and Complications", Clinical Cardiology, 11(5): 318-324, May 1988. Abstract.
Leung et al. "Feasibility of an Automatic Atrial and Ventricular Threshold Determination Using Transthoracic Using Impedance", Pace, 19(Part II): Abstract 263, p. 631, Apr. 1996.
Luepker et al. "Transthoracic Electrical Impedance: Quantitative Evaluation of a Non-Invasive Measure of Thoracic Fluid Volume", American Heart Journal, 85(1): 83-93, Jan. 1973.
Mai et al. "Enhanced Rate Response Algorithm for Orthostatic Compensation Pacing", Pacing and Clinical Electrophysiology, 23(11/Pt. 2): 1809-1811, Nov. 2000.
Mccarty et al. "Assessment of Pulmonary Edema in Acute Congestive Heart Failure With Impedance Cardiography", p. 1.
Mcnamee et al. Peribronchial Electrical Admittance Measures Lung Edema and Congestion in the Dog, Journal of Applied Physiology,49(2): 337-341, 1980. Abstract.

Newell et al. "Assessment of Acute Pulmonary Edema in Dogs by Electrical Impedance Imaging", IEEE transactions on bio-medical engineering ,43(2):133-138, Feb. 1996. Abstract.
Nierman et al. "Evaluation of Transthoracic Bioelectrical Impedance Analysis in Monitoring Lung Water During Diuresis", Applied Cardiopulmonary Pathophysiology, 7(1):57-62, 1997.
Nierman et al. "Transthoracic Bioimpedance Can Measure Extravascular Lung Water in Acute Lung Injury1", Journal of Surgical Research, 65: 101-108, 1996.
Noble et al. "Diuretic Induced Change in Lung Water Assessed by Electrical Impedance Tomography", Physiological measurement, 21(1):155-163, Feb. 2000. Abstract.
Nukiwa et al. "Responses of Serum and Lung Angiotensin-Converting Enzyme Activities in the Early Phase of Pulmonary Damage Induced by Oleic Acid in Dogs", The American review of respiratory disease, 126(6):1080-1086, Dec. 1982.
Petersen et al. "Cardiac Pacing for Vasovagal Syncope: A Reasonable Therapeutic Option?", Pacing Clin Electrophysiol., 20(3 pt 2): 824-826, Mar. 1997. Abstract.
Petersen et al. "Electrical Impedance Changes in Thoracic Fluid Content During Thoracentesis", Clinical physiology, 14(4):459-466, Jul. 1994. Abstract.
Platia et al. "Time Course of Transvenous Pacemaker Stimulation Impedance, Capture Threshold, and Electrogram Amplitude", Pacing and clinical electrophysiology, 9(5):620-625, 1986.
Pomerantz et al. "Transthoracic Electrical Impedance for the Early Detection of Pilmonary Edema", Surgery, 66(1): 260-268, Jul. 1969.
Raaijmakers et al. "Estimation of Non-Cardiogenic Pulmonary Oedema Using Dual-Frequency Electrical Impedance", Medical & biological engineering & computing, 36(4):461-466, Jul. 1998. Abstract.
Raggueneau et al. "Monitoring of Intracellular and Extracellular Hydric Compartments by Body Impedance", Anesth. Anal. Rean, 36:439-443, 1979.
Ramos et al. "Transthoracic Electric Impedance", Minnesota Medicine, p. 671-676, Sep. 1975.
Rosborough et al. "Electrical Therapy for Pulseless Electrical Activity", NASPE, 23(4), Part II:591, Apr. 2000.
Saunders "The Use of Transthoracic Electrical Bioimpedance in Assessing Thoracic Fluid Status in Emergency Department Patients", Amrican Journal of Emergency Medicine, 6(4):337-340, Jul. 1988.
Schuster et al. "Application of Impedance Cardiography in Critical Care Medicine", Resuscitation, 11(3-4): 255-274, Mar. 1984.
Schwartzman et al. "Serial Defibrillation Lead Impedance in Patients With Epicardial and Nonthoracotomy Lead System", Journal of Cardiovascular Electrophysiology, 7(8): 697-703, Aug. 1996.
Shochat et al. "Internal Thoracic Impedance Monitoring: A New Prospect in Acute Heart Failure", European Heart Journal, 25:72, Aug. 2004.
Shoemaker et al. "Multicenter Trial of a New Thoracic Electrical Bioimpedance Device for Cardiac Output Estimation", Critical Care Medicine, 22(12): 1907-1912, Dec. 1994. Abstract.
Smith et al. "Canine Thoracic Electrical Impedance With Changes in Pulmonary Gas and Blood Volumes", Journal of applied physiology, 53(6):1608-1613, Dec. 1982. Abstract.
Spinale et al. "Noninvasive Estimation of Extravascular Lung Water Using Bioimpedance", Journal of Surgical Research, 47(6):535-540, Dec. 1989. Abstract.
Spinelli et al. "Method and System for Treatment of Neurocardiogenic Syncore".
Sra et al. "Cardiac Pacing During Neurocardiogenic (Vasovagal) Syncope", J Cardiovasc Electrophysiol., 6(9): 751-760, Sep. 1995. Abstract.
Stadler et al. "Automated Detection of Decreases in Intrathoracic Impedance to Predict CHF Hospitalization", 26(4 pt II):932, Apr. 2003.
Stahmann et al. "Improved Sensitivity and Specificity of Pulmonary Edema Detection When Using Transthoracic Impedance", U.S. Appl. No. 11/126,723, 64 Pgs., May 2005. Abstract.
Stanb "The Measurement of Lung Water Content", Journal of Microwave Power, 18(3):259-263, Sep. 1983.

(56) References Cited

OTHER PUBLICATIONS

Tang "Assessment of Total Body Water Using Bioelectrical Impedance Analysis in Neonates Receiving Intensive Care", Archives of Disease in Childhood. Fetal and Neonatal Edition, 77(2): F123-F126, Sep. 1997.
Tempel et al. "Transthoracic Electrical Impedance in Anaesthesia and Intensive Care", Resuscitation, 6(2):97-105, 1978.
Thakur et al. "Pericardial Effusion Increases Defibrillation Energy Requirement", Pace, 16(6):1227-1230, Jun. 1993.
Vainshtein et al. "The Functioning of the Cerebral Circulation System in Hyperthermia in rabbits", p. 1608-1614.
Van de water et al. "Monitoring the Chest With Impedance", Chest, 64(5):597-603, Nov. 1973.
Wang et al. "Impedance Based Prediction of CHF Admission Precedes Symptoms in Heart Failure Patients", Heartrythym, 1(Suppl 1):S213, 2004.
Wang et al. "Multiple Sources of the Impedance Cardiogram Based on 3-D Finite Difference Human Thorax Models", IEEE Transactions on Biomedical Engineering, 42(2):141-148, Feb. 1995. Abstract.
Wang et al. "Prediction of CHF Hospitalization by Ambulatory Intrathoracic Impedance Measurement in CHF Patients is Feasible Using Pacemaker or ICD Lead Systems", Pacing and Clinical Electrophysiology, 26(4 pt II):959, Apr. 2003.
Wuerz et al. "Effects of Prehospital Medications on Mortality and Length of Stay in Congestive Heart Failure", Annals of Emergency Medicine, 21(6): 669-674, Jun. 1992. Abstract.
Yu et al. "Changes in Device Based Thoracic Impedance in Decompensating Congestive Heart Failure", Circulation, 104(17 Supplement): II-419, 2001.
Yu et al. "Correlation of Device-Based Intra-Thoracic Impedance and Patient Fluid Status During Intravenous Diuretic Therapy in Acute CHF", European Heart Journal, 23:158, 2002.
Yu et al. "Device-Based Intra-Thoracic Impedance Correlates With Fluid Status and Provides Automaticed Prediction of CHF Hospitalization", Journal of Cardiac Failure, 10(4 Suppl):S113, 2004.
Yu et al. "Early Warning of CHF Hospitalization by Intra-Thoracic Impedance Measurement in CHF Patients With Pacemakers", Pace, 24(4 pt II):527, 2002.
Yu et al. "Early Warning of CHF Hospitalization by Intra-Thoracic Impedance Measurement in CHF Patients With Pacemakers", Pacing and Clinical Electrophysiology, PACE, 24(19), Apr. 2001.
Yu et al. "Impedance Measurements From Implanted Devices Provide Automated Prediction of CHF Hospitalization", European Heart Journal, 25:27, Aug. 2004.
Yu et al. "Intrathoracic Impedance: A Surrogate Measure of Fluid Retention and Predictor of Hospitalization in Patients With Heart Failure", Journal of the American Collede of Cardiology, 4(6 Supplement A):1206-1270, 2003. Abstract.
Zellner et al. "Bioimpedance: A Novel Method for the Determination of Extravascular Lung Water", Journal of Surgicl Research, 48(5):454-459, May 1990. Abstract.
Zima "Intracardiac Impedance in Biventricular Electrode Configuration for Left Ventricular Volume Monitoring", European Heart Journal, 25:165, Sep. 2004.
Notice of Allowance dated Sep. 29, 2006 from U.S. Appl. No. 10/411,795, 4 pages.
Office Action Response dated Jul. 13, 2006 from U.S. Appl. No. 10/411,795, 22 pages.
Office Action dated Apr. 16, 2006 from U.S. Appl. No. 10/411,795, 5 pages.
Office Action Response dated Jan. 17, 2006 from U.S. Appl. No. 10/411,795, 22 pages.
Office Action dated Nov. 1, 2005 from U.S. Appl. No. 10/411,795, 5 pages.
Notice of Allowance dated Sep. 21, 2006 from U.S. Appl. No. 09/919,483, 4 pages.
Notice of Allowance dated Feb. 24, 2006 from U.S. Appl. No. 09/919,483, 4 pages.

Notice of Allowance dated Mar. 22, 2005 from U.S. Appl. No. 09/919,483, 4 pages.
Office Action Response dated Jan. 3, 2005 from U.S. Appl. No. 09/919,483, 13 pages.
Office Action dated Oct. 4, 2004 from U.S. Appl. No. 09/919,483, 5 pages.
Office Action Response dated Dec. 29, 2003 from U.S. Appl. No. 09/919,483, 12 pages.
Office Action dated Sep. 22, 2003 from U.S. Appl. No. 09/919,483, 4 pages.
Notice of Allowance dated Feb. 6, 2003 from U.S. Appl. No. 09/919,483, 5 pages.
Office Action Response dated Nov. 27, 2002 from U.S. Appl. No. 09/919,483, 9 pages.
Office Action dated Aug. 22, 2002 from U.S. Appl. No. 09/919,483, 4 pages.
Adamicza et al., Changes in transthoracic electrical impedance during endotoxemia in dogs, Acta Physiol Hung., 85(4), 1997-98, 291-302. (abstract only).
Adamicza et al, Investigation of the thoracic electrical impedance during endotoxemia in dogs, Acta Chir Hung, 36(1-4), 1997, 1-3. (abstract only).
Alt et al. Control of Pacemaker rate by impedance-based respitory minute ventilation, Chest, 92(2), Aug. 1987, 247-252.
Baarends et al., Body-water compartments measured by bio-electrical impedance spectroscopy in patients with chronic obstructive pulmonary disease, Clinical Nutrition, 17(1), Feb. 1998, 15-22. (abstract only).
Belalcazar et al., Improved lung edema monitoring with coronary vein pacing leads: a simulation study, Physiological Measurement, vol. 25, 2004, pp. 475-487. (abstract only).
Belalcazar et al., Improved lung edema monitoring with coronary vein pacing leads, Pacing and clinical electrophysiology, 26(4 pt II), Abstract 18, Apr. 2003, 933. (no copy).
Berman et al., Tranthoracic electrical impedance s a guide to intravascular overload, Arch Surg., 102(1), Jan. 1971, pp. 61-64. (no copy).
Bradbury et al. Assessment of the sensitivity of bioimpedance to volume changes in body water, Pediatr Nephrol., 9(3), Jun. 1995, 337-40. (abstract only).
Campbell et al. Clinical applications of electrical impedance tomography in the monitoring of changes in intrathoracic fluid volumes, Physiol Meas, vol. 15, 1994, A217-A222. (abstract only).
Campbell et al., Detection of changes in inthrathoracic fluid in man using electrical impedance tomography, Clinical Science, vol. 87, 1994, pp. 97-101. (abstract only).
Charach et al., Transthoracic monitoring of the impedance of the right lung in patients with cardiogenic pulmonary edema, Crit Care Med, 29(6), Jun. 2001, pp. 1137-1144. (abstract only).
Chiolero et al., Assessment of changes in body water by bioimpedance in acutely ill surgical patients, Intensive Care medicine, 18(6), 1992, 322-6. (abstract only).
Defaye et al., Automatic recognition of abnormal respiratory events during sleep by a pacemaker transthoracic impedance sensor, Journal of Cardiovascular Electrophysiology, 15(9), Sep. 2004, 1034-40. (abstract only).
Denniston et al., Factors influencing the measurement of stroke volume by electrical impedance, Phsiology, (1372-1377), Cardiac Output, Abstract No. 1373, 463. (no copy).
Denniston et al., Measurement of pleural effusion by electrical impedance, Journal of Applied Physiology, 38(5), May 1975, 851-7. (abstract only).
Ebert et al., The use of thoracic impedance for determining thoracic blood vol. changes in man, Aviat Space Environ Med, 57(1), Jan. 1986, pp. 49-53. (abstract only).
Fein et al., Evaluation of transthoracic electrical impedance in the diagnosis of pulmonary edema, Circulation, vol. 60, No. 5, Nov. 1978, pp. 1156-1160.
Foreman et al., Intra-thoracic impedance: a surrogate measure of thoracic fluid—fluid accumulation status trial (FAST), Journal of Cardiac Failure, 19(4 Supp), Abstract 251, 2004, S86. (no copy).

(56) References Cited

OTHER PUBLICATIONS

Forro et al. Total body water and ECFV measured using bioelectrical impedance analysis and indicator dilution in horses, Journal of Applied Physiology, 89(2), Aug. 2000, 663-71.
Frerichs I et al, Electrical impedance tomography in monitoring experimental lung injury, Intensive Care Med, 24(8), Aug. 1998, 829-36. (abstract only).
Garland et al., Measurement of extravascular lung water in hemodialysis patients using blood ultrasound velocity and optical density dilution, ASAIO Journal 2002, 48(4), Jul.-Aug. 2002, 398-403. (abstract only).
Goovaerts et al., Microprocessor-based system for measurement of electrical impedances during haemodialysis and in postoperative care, Medical & Biological Engineering & Computing, vol. 26, Jan f1988, pp. 75-80. (abstract only).
Gotschall et al., Biolectric impedance as an index of thoracic fluid, Aviation Space and Environmental Medicine, 70(1), Jan. 1999, 58-61. (abstract only).
Grimbert et al., Pulmonary water and thoracic impedance. Evaluation of a measurement technic, Annales de L'anesthesiologie Francaise, 16 Spec No. 203, French, 1975, 157-63. (abstract only).
Harris et al., Applications of applied potential tomography (APT) in respiratory medicine, Clinical Physics and Physiological Measurement, 8 Supp A, 1987, 155-65. (no copy).
Hoon et al., Changes in transthoracic electrical impedance at high altitude, British Heart Journal, vol. 39, 1977, pp. 61-66. (abstract only).
Hull et al, The transthoracic impedance method for the determination of the degree and change in extravascular water, Acta Tuberc. Pneumol. Belg. 68/4, 1977, pp. 369-377. (no copy).
Hull et al, Transthoracic electrical impedance: artifacts associated with electrode movement, Resuscitation, vol. 6, pp. 115-124. (abstract only).
Ishibe et al., Transthoracic electrical impedance method for measurement of pulmonary edema in vivo, Masui: 27(13), Japanese, Dec. 1978, 1559-67. (no copy).
Joekes et al., Impedance Cardiography—Its value in an intensive care unit, D) Materials et techniques/Cardiocirculatory Equipment and Technics, Abstract No. 141, p. 1. (no copy).
Keller et al., Monitoring of pulmonary fluid volume and stroke volume by impedance cardiography in patients on hemodialysis, Chest, vol. 72, No. 1, Jul. 1977, pp. 56-62.
Khan et al., Quantitative electrical-impedance piethysmography for pulmonary oedema, Medical & Biological Engineering & Computing, vol. 15, Nov. 1977, pp. 627,633. (abstract only).
Kiesler et al., Impedance cardiography by use of a spot-electrode array to track changes in cardiac output in anesthetized dogs, Journal of the American Veterinary Medical Association, 196(11), Jun. 1, 1990, 1804-10.
Koizumi, Changes of transthoracic impedance (zinf 0 and deltaz) in newborn infants, Acta Neonatol. Jpn, 14(3), 1978, 335-340. (no copy).
Kunst et al., Electrical impedance tomography in the assessment of extravascular lung water in noncardiogenic acute respiratory failure, Chest, 116(6), Dec. 1999, 1695-702.
Kusumoto et al., Medical Progress: Cardiac Pacing, New England Journal of Medicine, 334(2), Jan. 11, 1996, pp. 86-98.
Larsen et al., Influence of furosemide and body posture on transthoracic electrical impedance in AMI, Chest, 90(5), 733-7, Nov. 1986.
Lau et al., Rate-responsive pacing with a pacemaker that detects respiratory rate (Biorate): clinical advantages and complications, Clin Cardiol, 11(5), May 1988, pp. 318-324. (abstract only).
Lau, The range of sensors and algorithms used in rate adaptive cardiac pacing, Pacing and clinical electrophysiology: PACE, 15(8), Aug. 1992, 1177-211. (abstract only).
Leung et al., Feasibility of an automatic atrial and ventricular threshold determination using thransthoracic using impedance, PACE, vol. 19, part II, Abstract 263, Apr. 1996. (no copy).
Luepker et al., Transthoracic Electrical Impedance: Quantitative Evaluation of a Non-Invasive Measure of Thoracic Fluid Volume, American Hearth Journal, vol. 85, No. 1, Jan. 1973, pp. 83-93. (no copy).
Mai et al., Enhanced Rate Response Algorithm for Orthostatic Compensation Pacing, Pace, 23, Naspe Abstracts, Abstract No. 678, p. 722, Apr. 2000. (abstract only).
McCarty et al., Assessment of pulmonary edema in acute congestive heart failure with impedance cardiography, Journal Am Osteopath Assoc, 74(9), May 1975, 879. (no copy).
McNamee et al., Peribronchial electrical admittance measures lung edema and congestion in the dog, Special Communications, Electrical Admittance and Pulmonary Edema, pp. 337-341. (abstract only).
Medtronic announces European release of innovative InSyne Sentry Cardiac Resynchronization Therapy Defibrillator, 2004.
Medtronic: InSync Sentry 7298: Dual chamber implantable cardioverter defibrillator with cardiac resynchronization therapy (VVE-DDR) and Opti-Vol Fluid Monitoring: Reference Manual, www.medtronic.com.
Newell et al., Assessment of acute pulmonary edema in dogs by electrical impedance imaging, IEEE Transactions on Biomedical Engineering, 43(2), Feb. 1996, 133-138. (abstract only).
Nieman et al., Evaluation of transthoracic bioelectrical impedance analysis in monitoring lung water during diuresis, Applied Cardiopulmonary Pathophysiology, 7(1), 1997, 57-62. (no copy).
Nierman et al., Transthoracic bioimpedance can measure extravascular lung water in acute lung injury 1, Journal of Surgical Research 65, Article No. 0350, 1996, pp. 101-108. (abstract only).
Noble et al., Diuretic induced change in lung water assessed by electrical impedance tomography, Physiol Meas., 21(1), Feb. 2000, 155-63. (abstract only).
Nukiwa et al., Responses of serum and lung angiotensin-converting enzyme activities in the early phase of pulmonary damage induced by oleic acid in dogs, Lung Damage by Oleic Acid and Ace Change, pp. 1080-1086. (abstract only).
Petersen et al., Cardiac pacing for vasovagal syncope: a reasonable therapeutic opinion?, Pacing Clin Electrophysiol, 20(3 pt 2), Mar. 1997, pp. 824-826. (abstract only).
Petersen et al., Electrical impedance measure changes in thoracic fluid content during thoracentesis, Clin Physiol., 14(4), Jul. 1994, 459-66. (no copy).
Platia, Time course of transvenous pacemaker stimulation impedance, capture threshold, and electrogram amplitude, Washington DC, Sep./Oct. 19, pp. 620-625. (abstract only).
Pomerantz et al., Transthoracic electrical impedance for the early detection of pulmonary edema, Surgery, 66(I), Jul. 1969, pp. 260-268. (no copy).
Raaijmakers et al., Estimation of non-cardiogenic pulmonary oedema using dual-frequency electrical impedance, Medical & Biological Engineering & Computing, 36(4), Jul. 1998, 461-6. (abstract only).
Raggueneau et al., Monitoring of intracellular and extracellular hydric compartments by body impedance, Anesth Anal. Rean, vol. 36, 1979, pp. 439-443. (no copy).
Ramos et al., Transthoracic electric impedance, Minnesota Medicine, Sep. 1975, pp. 671-676. (no copy).
Rosborough et al., Electrical therapy for pulseless electrical activity, NASPE,23(4), Part II, Abstract, Apr. 2000, 591. (no copy).
Saunders, The use of transthoracic electrical bioimpedance in assessing thoracic fluid status in emergency department patients, American Journal of Emergency Medicine, vol. 6, No. 4, Jul. 1988, pp. 337-340. (abstract only).
Schuster et al., Application of impedance cardiography in critical care medicine, Resuscitation, vol. 11, 1984, pp. 255-274. (abstract only).
Schwartzman et al., Serial defibrillation lead impedance in patients with epicardial and nonthoracotomy lead systems, Journal of Cardiovascular Electrophysiology, vol. 7 No. 8, Aug. 1996, pp. 697-703. (abstract only).
Shochat et al., Internal thoracic impedance monitoring: a new prospect in acute heart failure, European Heart Journal, 25(Supp), Aug.-Sep. 2004, p. 72-72. (no copy).

(56) References Cited

OTHER PUBLICATIONS

Shoemaker et al., Multicenter trial of a new thoracic electrical bioimpedance device for cardiac output estimation, Crit Care Med, 22(12), Dec. 1994, pp. 1907-1912. (no copy).
Smith et al., Canine thoracic electrical impedance with changes in pulmonary gas and blood volumes, Journal of Applied Physiology, 53(6), Dec. 1982, 1608-13. (abstract only).
Spinale et al., Noninvasive estimation of extravascular lung water using bioimpedance, The Journal of Surgical Research, 47(6), Dec. 1989, 535-40. (abstract only).
Sra et al., Cardiac pacing during neurocardiogenic (vasovagal) syncope, J Cardiovasc Electrophysiol, 6(9), Sep. 1995, pp. 751-760. (abstract only).
Stadler et al., Automated detection of decreases in intrathoracic impedance to predict CHF hospitalization, Abstract 263, 26(4 pt II), Abstract 16, Apr. 2003, 932. (no copy).
Staub, The measurement of lung water content, the Journal of Microwave Power, 18(3), Sep. 1983, 259-63. (abstract only).
Tang, Assessment of total body water using bioelectrical impedance analysis in neonates receiving intensive care, Arch Dis Child Fetal Neonatal Ed., 77(2), Sep. 1997, F123-6.
Tempel et al., Transthoracic electrical impedance in anaesthesia and intensive care, Resuscitation, 6(2), 1978, 97-105. (no copy).
Thakur et al. Pericardial effusion increases defibrillation energy requirement, PACE, vol. 16, Jun. 1993, 1227-1230. (abstract only).
Vainshtein et al., The functioning of the cerebral circulation system in hyperthermia in rabbits, 1608-1614. (no copy).
Van de Water et al., Monitoring the chest with impedance, Chest, vol. 64, No. 5, Nov. 1973, 597-603.
Wang et al., Impedance based prediction of CHF admission precedes symptoms in heart failure patients, Heartrhythm:the official journal of the heart rhythm society, 1(Supp 1), Abstract 679, 2004, S213. (no copy).
Wang et al., Multiple sources of the impedance cardiogram based on 3D finite difference human thorax models, IEEE Transactions on Biomedical Engineering, vol. 42, No. 2, Feb. 1995, 141-148. (abstract only).
Wang et al., Prediction of CHF hospitalization by ambulatory intrathoracic impedance measurement in CHF patients is feasible using pacemaker or ICD lead systems, Pacing and Clinical Electrophysiology, 26(4 pt II), Abstract 123, Apr. 2003, 959. (no copy).
Wuerz et al., Effects of prehospital medications on mortality and length of stay in congestive heart failure, Annals of Emergency Medicine, 21(6), Jun. 1992, pp. 669-674. (abstract only).
Yu et al., Changes in device based thoracic impedance in decompensating congestive heart failure, Circulation, 104(17 supplement, Abstract 1994, 2001, 11-419. (no copy).
Yu et al., Correlation of device-based intrapthoracic impedance and patient fluid status during intravenous diuretic therapy in decompensating congestive heart failure, Circulation, 104(17 supplement, 2002, 158. (no copy).
Yu et al., Device-based intra-thoracic impedance correlates with fluid status and provides automatived prediction of CHF hospitalization, Journal of Cardiac Failure, 10(4 Suppl), Abstract 354, 2004, S113. (no copy).
Yu et al., Early warning of CHF hospitalization by intra-thoracic impedance measurement in CHF patients with pacemakers, Pacing and Clinical Electrophsiology (PACE), 24(4 pt II), Abstract 19, 2002, 527. (no copy).
Yu et al., Impedance measurements from implanted devices provide automated prediction of CHF hospitalization, European Heart Journal, 25(Supp), Aug.-Sep. 2004, 27-27. (no copy).
Yu et al., Intrathoracic impedance: a surrogate measure of fluid retention and predictor of hospitalization in patients with heart failure, Journal of the American College of Cardiology, 41(6 Supplement A), Abstract 2106-70, 2003, 210A.
Zellner et al., Bioimpedance: a novel method for the determination of extravascular lung water, The Journal of Surgical Research, 48(5), May 1990, 454-9. (abstract only).
Zima, Intracardiac impedance in biventricular electrode configuration for left ventricular volume monitoring, European Heart Journal, 25(Supp), Aug.-Sep. 2004, 165-165. (no copy).
Forro et al. "Total Body Water and ECFV Measured Using Bioelectrical Impedance Analysis and Indicator Dilution in Horses", Journal of Applied Physiology, 89(2):663-671, Aug. 2000.
Grimbert et al. "Pulmonary Water and Thoracic Impedance Evaluation of a Measurement Technic", Annales de l'anesthésiologie franoise, 16 Spec (2-3):157-163, 1975. Abstract.
Larsen et al. Influence of Furosemide and Body Posture on Transthoracic Electrical Impedance in AMI, Chest, 90(5):733-737, Nov. 1986.
Stahmann "Thoracic Impedance Detection With Blood Resistivity Compensation", U.S. Appl. No. 10/921,503, filed Aug. 19, 2004, 38 Pgs. Abstract.

\* cited by examiner

CONTRACTILITY MODULATION BASED ON IMPEDANCE SIGNAL

CROSS-REFERENCE TO RELATED APPLICATION(S)

This application is a continuation of U.S. patent application Ser. No. 11/673,699 filed on Feb. 12, 2007 now abandoned which is a continuation of U.S. patent application Ser. No. 10/411,795, filed on Apr. 11, 2003, now issued as U.S. Pat. No. 7,177,681, which is a continuation of U.S. patent application Ser. No. 09/919,483, filed on Jul. 31, 2001, now issued as U.S. Pat. No. 7,191,000, the specifications of which are incorporated herein by reference.

This application is related to the following co-pending and commonly assigned patent applications: U.S. patent application Ser. No. 09/832,365 entitled "CARDIAC RHYTHM MANAGEMENT SYSTEM FOR HYPOTENSION," filed on Apr. 10, 2001, now issued as U.S. Pat. No. 6,912,420; U.S. patent application Ser. No. 09/879,665 entitled CARDIAC RHYTHM MANAGEMENT SYSTEM ADJUSTING RATE RESPONSE FACTOR FOR TREATING HYPTOTENSION, filed on Jun. 12, 2001, now issued as U.S. Pat. No. 6,907,288; and to U.S. patent application Ser. No. 09/917,259 entitled "METHOD AND SYSTEM FOR TREATMENT OF NEUROCARDIOGENIC SYNCOPE," filed on Jul. 27, 2001, now issued as U.S. Pat. No. 6,748,271, the specifications of which are incorporated herein by reference in their entirety.

TECHNICAL FIELD

This document relates generally to cardiac rhythm management systems and particularly, but not by way of limitation, to such a system for detecting and/or treating edema.

BACKGROUND

Excess fluid buildup ("edema") in a subject may be associated with many diseases. Edema results from inadequate or excessive response of homeostatic processes in the body. For example, acute pulmonary edema is a short-term fluid buildup in the lungs. In some people, such excess fluid buildup (also referred to as "decompensation") results from inadequate cardiac output of the heart, such as is associated with congestive heart failure ("CHF"). Pulmonary edema may occur late in the CHF disease process and, therefore, may have serious consequences. The fluid accumulation in the lungs may result in labored breathing and, in severe cases, may even result in death. For these and other reasons, there is a need to detect edema and, more importantly, to provide appropriate responsive therapy to treat edema and/or any underlying heart condition causing the edema.

SUMMARY

This document discusses a cardiac rhythm management system that detects edema. In response to an episode of detected edema, it initiates and/or adjusts a cardiac resynchronization therapy and/or a cardiac contractility modulation (CCM) therapy.

One example discusses a cardiac rhythm management system. The system includes an edema detection circuit to sense a condition correlative to edema in a subject. An electrical energy delivery circuit delivers electrical energy to the subject. A controller is coupled to the edema detection circuit to receive a detected edema indicator. The controller is also coupled to the energy delivery circuit to provide a control signal for timing delivery of the electrical energy to the subject. The controller includes a cardiac resynchronization therapy mode and a cardiac contractility modulation therapy mode. The controller is configured, in response to the detected edema indicator, to perform at least one of: initiating/adjusting the cardiac resynchronization therapy; and, initiating/adjusting the cardiac contractility modulation therapy. Other aspects of the invention will be apparent on reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
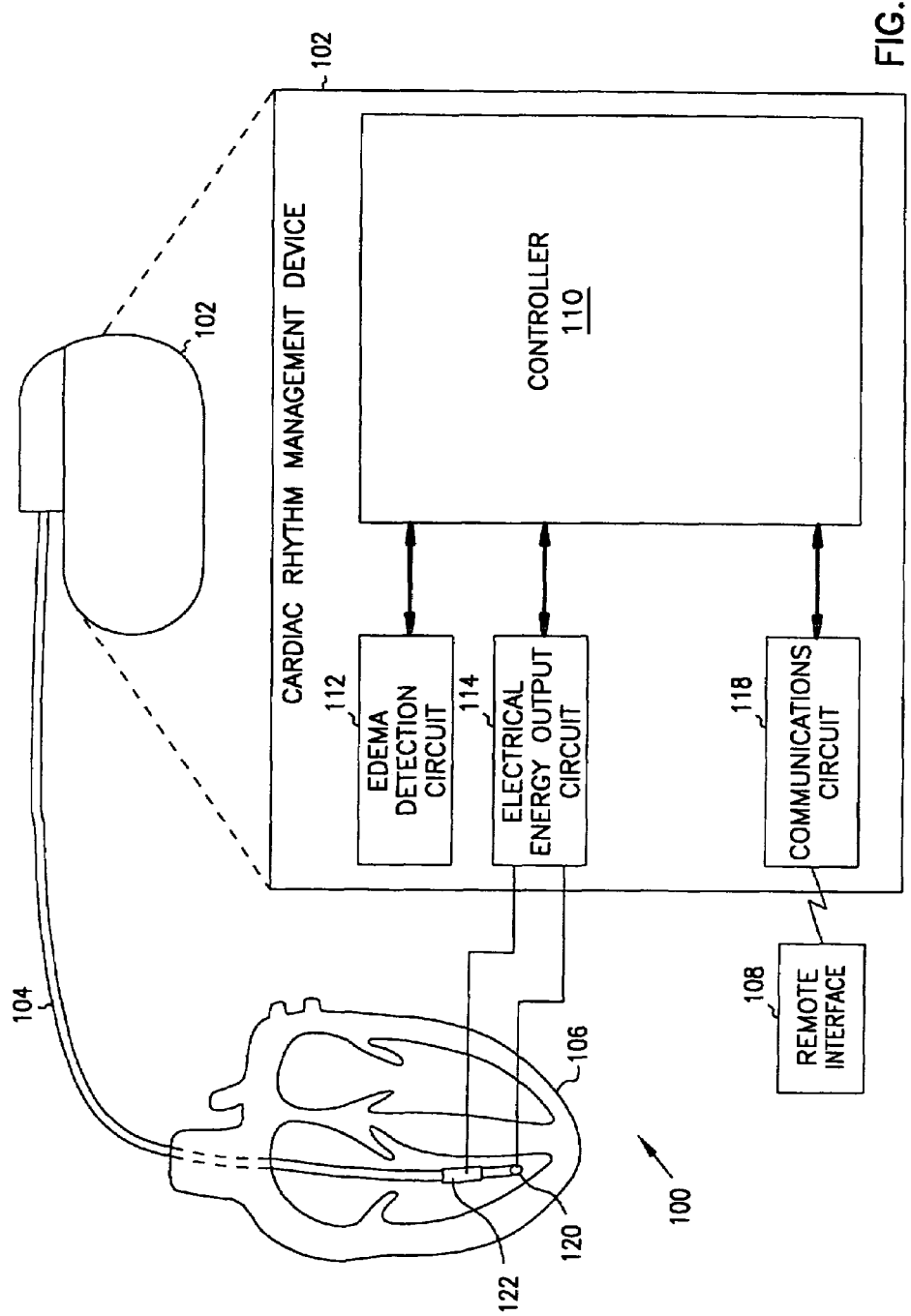
FIG. 1 is a block diagram example of portions of a cardiac rhythm management system and portions of an environment in which it is used.

FIG. 1 is a block diagram example of portions of one possible cardiac rhythm management system 100 and portions of an environment in which it is used. In this example, system 100 includes, among other things, a cardiac rhythm management device 102 and leadwire ("lead") 104. Leadwire 104 is coupled to device 102 for communicating one or more signals between device 102 and a portion of a living organism or other subject, such as heart 106. Some examples of device 102 include, among other things, bradycardia and antitachycardia pacemakers, cardioverters, defibrillators, combination pacemaker/defibrillators, cardiac resynchronization therapy devices, and drug delivery devices. Other examples of device 102 include any other implantable or external cardiac rhythm management apparatus capable of providing cardiac rhythm management therapy to heart 106. Such cardiac rhythm management therapy is not limited to managing cardiac rate. For example, cardiac rhythm management therapy also includes cardiac resynchronization therapy. Cardiac resynchronization therapy typically coordinates the spatial nature of a depolarization associated with a heart contraction in one or more heart chambers. While such cardiac resynchronization therapy may modify cardiac rate, it can also occur without any modification of the rate at which heart contractions occur. Some examples of cardiac resynchronization therapy include simultaneous or offset multichamber (e.g., biventricular) pacing and/or simultaneous or offset delivery of pacing pulses to multiple electrodes associated with a single heart chamber. Moreover, the cardiac rhythm management therapy discussed in this document also includes cardiac contractility modulation (CCM) therapy. CCM therapy includes delivering electrical energy to a portion of the heart during a refractory time period when that portion of the heart is relatively unlikely to contract in response to the received electrical energy. Therefore, CCM therapy need not adjust cardiac rate and, moreover, need not even evoke responsive heart contractions. System 100 may also include additional components such as, for example, an external or other remote interface 108 capable of communicating with device 102.

In this example, device 102 includes, among other things, a microprocessor or other controller 110 coupled to an edema detection circuit 112, an electrical energy output circuit 114, and a communication circuit 118. Communication circuit 118 is adapted for wireless or other communication with remote interface 108. Electrical energy output circuit 114 is coupled to one or more electrodes associated with any chamber(s) of heart 106, such as electrodes 120 and 122 of lead 104. Such electrodes deliver electrical pacing stimulations for evoking responsive heart contractions or for delivering cardiac contractility modulation ("CCM") energy pulses, which do not evoke responsive heart contractions, as discussed below.

In this example, edema detection circuit 112 detects a condition in the subject that is correlative to an episode of edema, and outputs a responsive edema indicator to controller 110. In one response to the detected edema, controller 110 initiates or adjusts a cardiac resynchronization therapy. In another response to the detected edema, controller 110 initiates or adjusts a CCM therapy. In a further example of operation, controller 110 communicates an indication of the detected edema through communication circuit 118 to remote interface 108 for visible display or for other user output.

Figure 2:
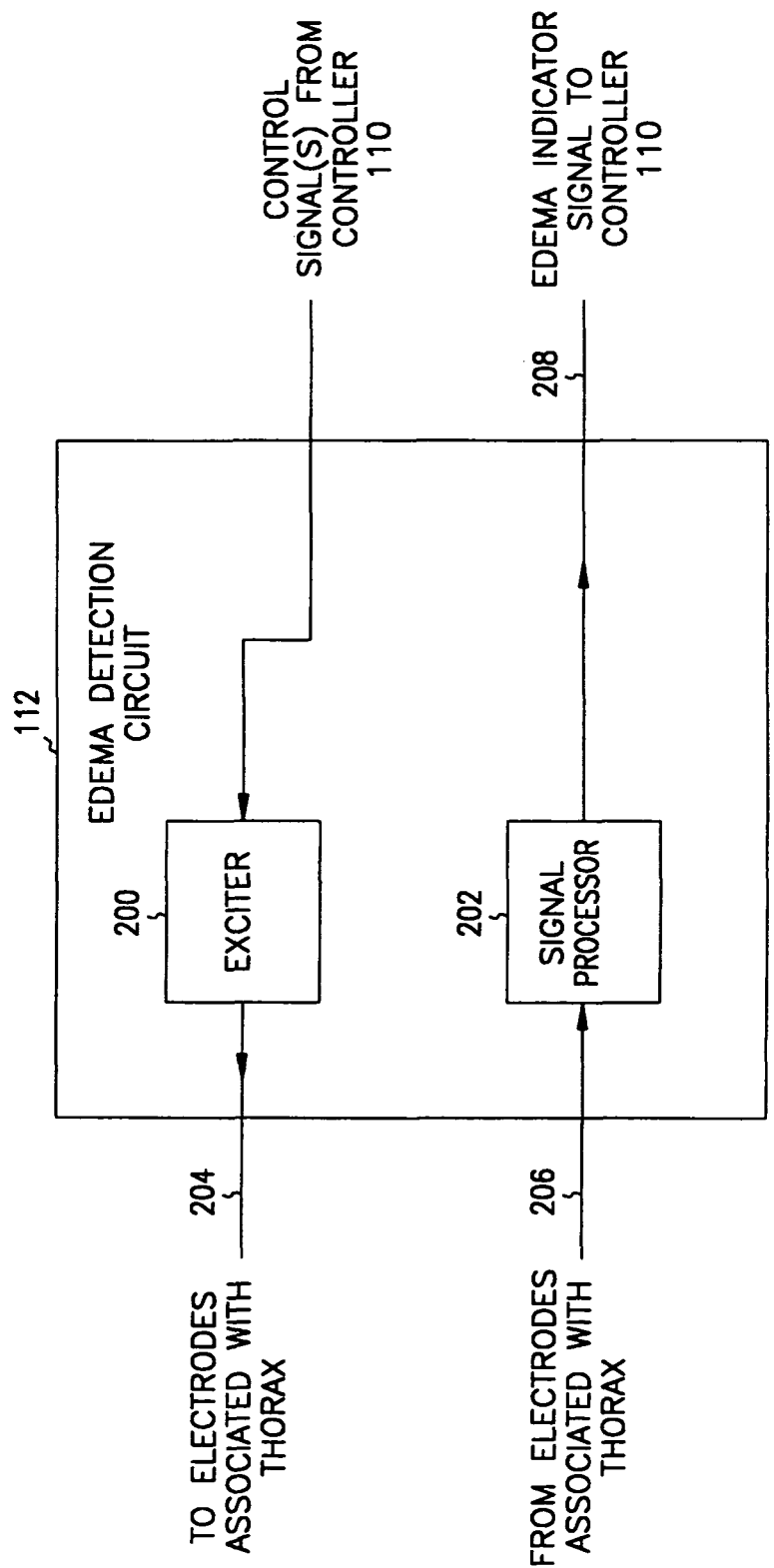
FIG. 2 is a block diagram example of one possible edema detection circuit.

FIG. 2 is a block diagram example of one possible edema detection circuit 112 that senses thoracic impedance to determine whether the edema condition is present. In this example, edema detection circuit includes exciter 200 and signal processor 202, both of which are coupled to electrodes associated with a portion of the subject's thorax. In this document, the term "thorax" refers to the subject's body other than the subject's head, arms, and legs. Exciter 200 provides, at node/bus 204, a test signal to the thorax, from which thoracic impedance is determined. Exciter 200 need not, and typically does not, stimulate tissue or muscle contractions in the thorax; it is referred to as an exciter because it provides a test excitation signal for determining impedance. Signal processor 202 receives from the thorax, at node/bus 206, signals responsive to the test signal provided by exciter 200. Signal processor 202 outputs, at node/bus 208, the edema indicator to controller 110.

The thoracic electrodes associated with exciter 200 may be different from the thoracic electrodes associated with signal processor 202. For example, one such suitable electrode configuration for sensing thoracic impedance includes the configuration of at least four electrodes for detecting thoracic impedance, such as discussed in Hauck et al. U.S. Pat. No. 5,284,136 entitled "DUAL INDIFFERENT ELECTRODE PACEMAKER," assigned to Cardiac Pacemakers, Inc., the disclosure of which is incorporated herein by reference in its entirety. However, a different number of electrodes (e.g., 2 or 3 electrodes, or more than 4 electrodes) could also be used. Therefore, in another example, one or more of the thoracic electrodes of edema detection circuit 112 is shared by both exciter 200 and signal processor 202.

In one example, exciter 200 and signal processor 202 cooperate to detect thoracic impedance using a high frequency carrier signal to provide the test stimulus that obtains the thoracic impedance response, as discussed in Hartley et al. U.S. Pat. No. 6,076,015 ("the Hartley et al. patent") entitled "RATE ADAPTIVE CARDIAC RHYTHM MANAGEMENT DEVICE USING TRANSTHORACIC IMPEDANCE," assigned to Cardiac Pacemakers, Inc., the disclosure of which is incorporated herein by reference in its entirety.

Figure 3:
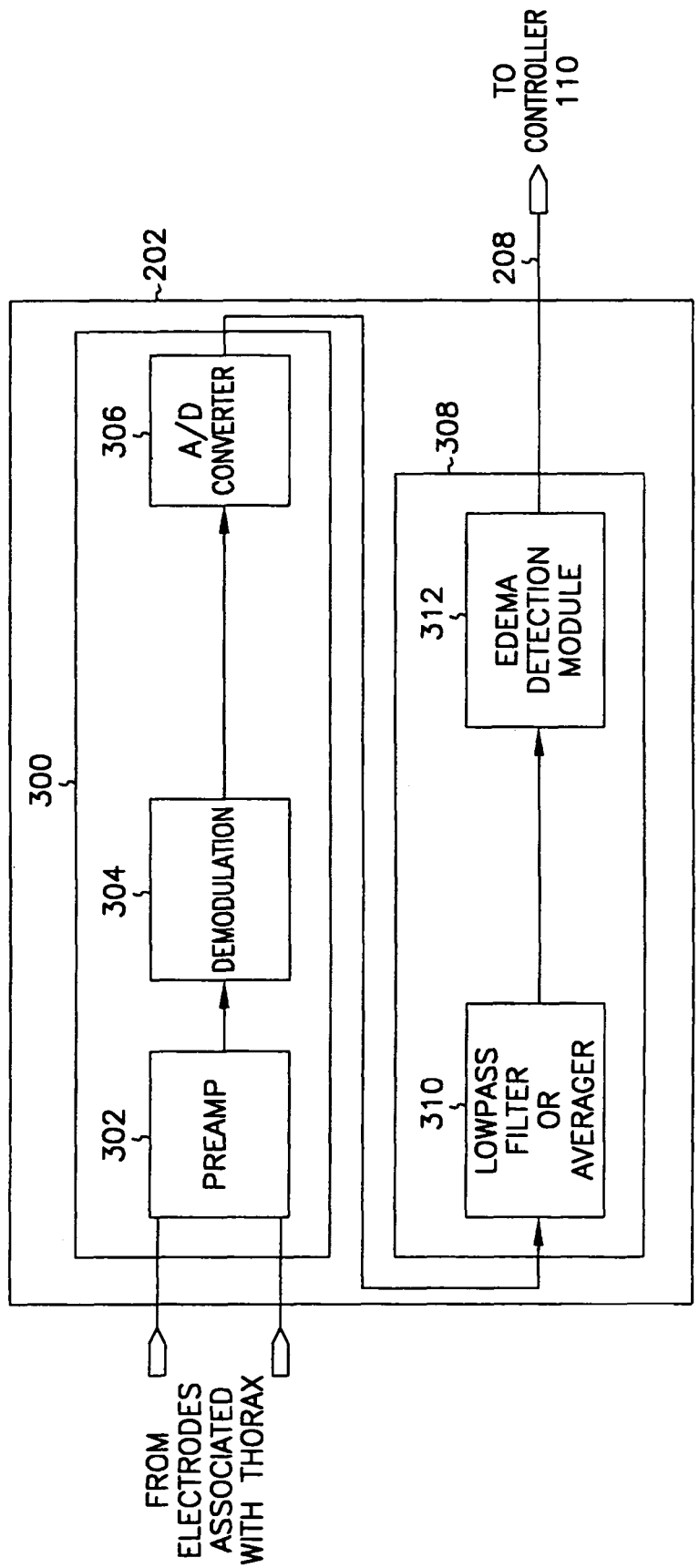
FIG. 3 is a block diagram example of portions of a possible signal processor.

FIG. 3 is a block diagram example of portions of a possible signal processor 202. The input signal from the thoracic electrodes, which is responsive to the test stimulus provided by exciter 200, is received by an analog signal processing circuit 300 at its preamplifier 302 circuit. A signal provided by an output of preamplifier 302 is received by a demodulator 304 circuit. Demodulator 304 demodulates the high frequency carrier signal to extract thoracic impedance information. A signal provided by an output of demodulator 304 is received by analog-to-digital (A/D) converter 306, where it is converted into a digital thoracic impedance signal. Suitable examples of preamplifier 302, demodulator 304, and A/D converter 306 are discussed in the Hartley et al. patent, which was above incorporated by reference in its entirety.

In this example, the digitized signal provided by A/D converter 306 undergoes further signal processing in the digital domain by digital signal processing circuit 308, which includes a lowpass filtering or averager 310 receiving the digital output signal from A/D converter 306. The digitized thoracic impedance signal is influenced not only by the amount of fluid in a subject's thorax, but also by the subject's heart beat (referred to as the "cardiac stroke" signal component) and the subject's breathing (also referred to as the "respiration" or "ventilation" component). Lowpass filter or averager 310 extracts the "dc" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz). The baseline component of the thoracic impedance signal provides information about the amount of fluid in the subject's thorax. A decrease in the baseline thoracic impedance indicates the thoracic fluid accumulation condition associated with edema. In providing the baseline thoracic impedance output signal, lowpass filter or averager 310 attenuates the higher frequency components of the thoracic impedance signal that are influenced by the patient's breathing (e.g., approximately between 0.05 Hz and 2.0 Hz inclusive) and heartbeat (e.g., approximately between 0.5 Hz and 10 Hz inclusive). Digital signal processing circuit 308 also includes an edema detection module 312 which determines whether the baseline impedance signal received from lowpass filter or averager 310 indicates that edema is present in the subject, and provides the resulting edema indicator at node 208 to controller 110.

Figure 4:
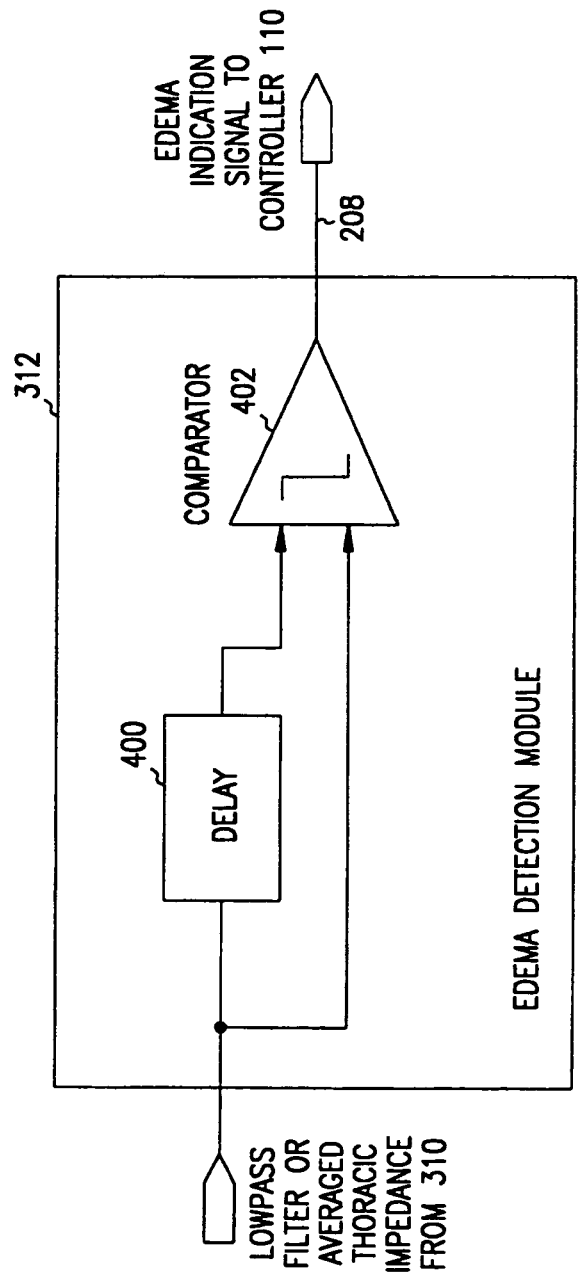
FIG. 4 is a block diagram example of one possible edema detection module.

FIG. 4 is a block diagram example of one possible edema detection module 312. It includes a delay 400 that outputs a long-term value of the lowpass-filtered thoracic impedance, that is, the baseline thoracic impedance including information about fluid shifts to and away from the thorax. Comparator 402 compares the substantially instantaneous and long-term values of the baseline thoracic impedance at its respective comparator inputs. If the substantially instantaneous baseline thoracic impedance is less than the long-term value of the baseline thoracic impedance by a predetermined threshold value, then comparator 402 provides a resulting signal, at node 208, that indicates that edema is present. Otherwise, the resulting signal at node 208 indicates that edema is not present.

Figure 5:
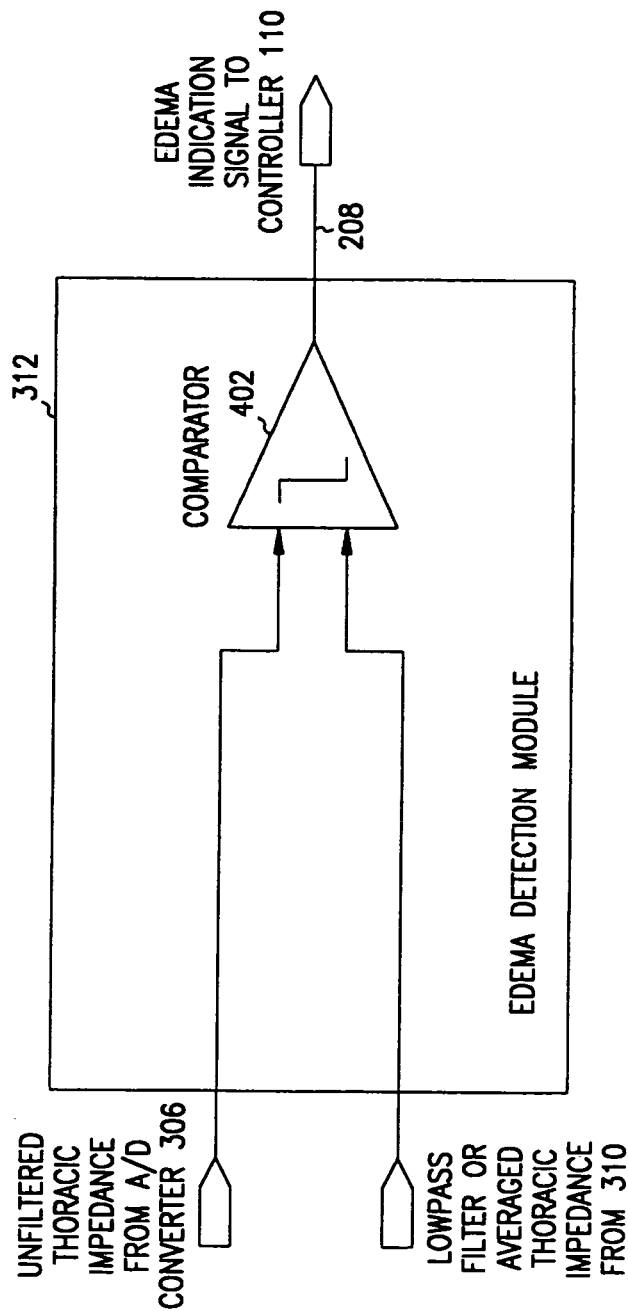
FIG. 5 is a block diagram example of an alternative edema detection module.

FIG. 5 is a block diagram example of an alternative edema detection module 312. In this example, comparator 402 compares the unfiltered thoracic impedance from the output A/D converter 306 to the lowpass-filtered thoracic impedance (i.e., the baseline thoracic impedance) from the output of lowpass filter or averager 310. If the unfiltered thoracic impedance from A/D converter 306 is less than the baseline thoracic impedance from lowpass filter or averager 310 by a predetermined threshold value, then comparator 402 provides the resulting signal, at node 208, that indicates that edema is present. Otherwise, the resulting signal at node 208 indicates that edema is not present.

Figure 6:
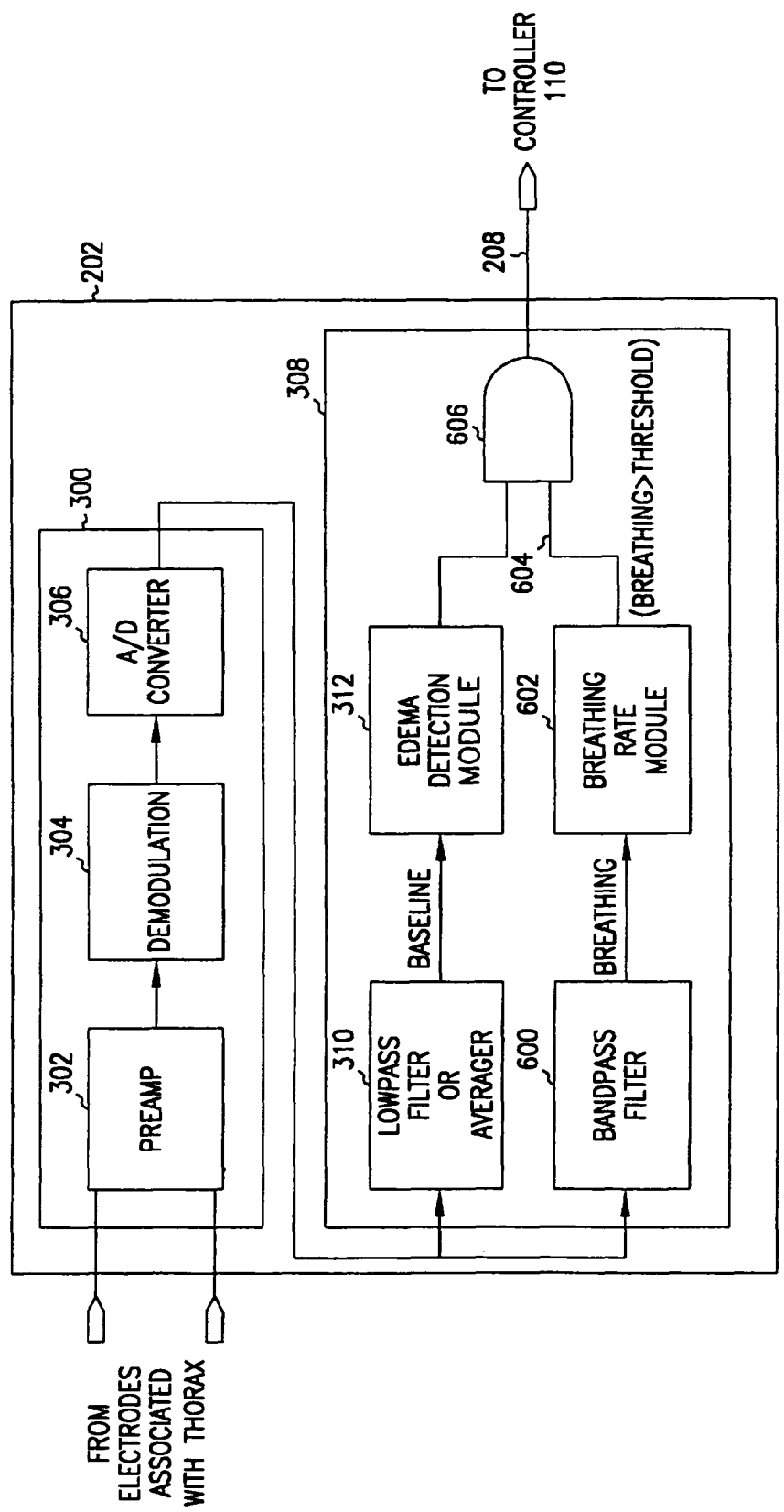
FIG. 6 is a block diagram example of an alternative signal processing circuit that determines whether edema is present based not only on the baseline thoracic impedance signal, but also on an additional breathing rate criterion.

FIG. 6 is a block diagram example of an alternative signal processing circuit 202 that determines whether edema is present based not only on the baseline thoracic impedance signal, but also on an additional breathing rate criterion. In the example of FIG. 6, the digitized thoracic impedance signal from A/D converter 306 is also received at an input of bandpass filter 600. Bandpass filter 600 attenuates frequencies outside the frequency range associated with the breathing component of the thoracic impedance signal (e.g., approximately between 0.05 Hz and 2.0 Hz inclusive). Bandpass filter 600 outputs a signal correlative to the subject's breathing, which is received at an input of breathing rate module 602. Breathing rate module 602 includes a fiducial point detector (e.g., zero-cross detector, level detector, peak detector, etc.) detecting a fiducial point on the breathing signal that occurs a known number of one or more times during breathing cycle (of inhaling and exhaling). A timer measures the time interval between respective successive fiducial points, from which the breathing rate is determined. A comparator compares the breathing rate to a threshold value that is approximately between 10 breaths per minute and 40 breaths per minute, such as about 25 breaths per minute. Breathing rate module 602 outputs at node 604 a digital signal indicating whether the breathing rate threshold is being exceeded. This signal is used (e.g., by AND gate 606) to qualify the signal output from edema detection module 312. Therefore, the edema-present indicator at node 208 is asserted only if both the baseline thoracic impedance indicates a fluid accumulation in the thorax and the breathing rate exceeds the threshold value.

In a further example, in which device 102 includes an activity sensor (such as, for example, an accelerometer), the signal output from edema detection module 312 is further qualified by a digital signal indicating whether the patient is resting. This is determined by comparing the activity level indicated by the activity sensor to a threshold value. The patient is deemed to be resting when the activity level is less than the threshold value. In such an example, AND gate 606 is implemented as a 3-input AND gate, with a first input receiving the output of edema detection module 312, a second input receiving the output of breathing rate module 602, and a third input receiving a signal, based on the comparison of the activity level to the threshold value, that is a logical "1" if the patient is resting. The output of the 3-input AND gate is communicated, at node 208, to controller 110. In this example, the edema-present indicator at node 208 is asserted only if both the baseline thoracic impedance indicates a fluid accumulation in the thorax and the resting breathing rate exceeds the threshold value.

Figure 7:
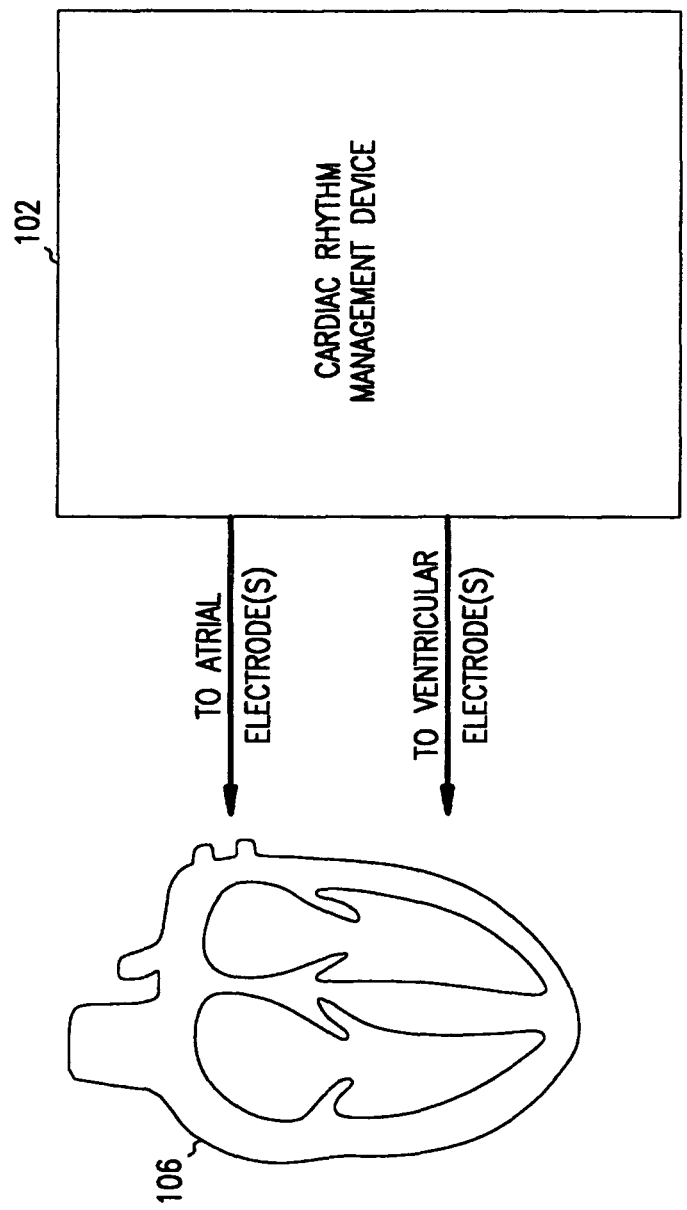
FIG. 7 is a block diagram example in which a cardiac rhythm management device is associated with a heart at both an atrium (right or left) and a ventricle (right or left).

When the edema indicator received at node 208 by controller 110 indicates that edema is present, controller 110 responds by initiating or adjusting a therapy provided to heart 106. In one example, controller 110 responds to an edema detection by initiating or adjusting a cardiac resynchronization therapy that coordinates the spatial nature of a depolarization associated with a heart contraction in one or more heart chambers. FIG. 7 is a block diagram example in which device 102 is associated with heart 106 at both an atrium (right or left) and a ventricle (right or left) for sensing and/or pacing atrial and/or ventricular heart contractions occurring during the same cardiac cycle (of an atrial and subsequent ventricular contraction). The atrial contraction and the subsequent ventricular contraction occurring during the same cardiac cycle are separated by a time interval that is referred to as an atrioventricular (AV) delay. In one example of adjusting a cardiac resynchronization therapy in response to detected edema, controller 110 adjusts the AV delay value stored in a memory location of controller 110. In one example, the AV delay value is programmable by the user to be approximately between 20 milliseconds and 200 milliseconds, such as about 100 milliseconds. In response to the detected edema, controller 110 incrementally adjusts, over a suitable period of time for allowing the edema to abate, the AV delay to a shorter or longer value until the edema abates or all possible AV delay values have been exhausted.

In an example of initiating a cardiac resynchronization therapy in response to the detected edema, controller 110 switches from pacing a single ventricle (e.g., the right ventricle) to biventricular pacing of electrodes associated with each of the right and left ventricles. One suitable electrode configuration for biventricular pacing includes at least one intravascular electrode in the right ventricle and at least one other intravascular electrode introduced into the coronary sinus and/or great cardiac vein into association with the left ventricle. The biventricular pacing includes simultaneous delivery of pacing stimuli to both ventricles. The biventricular pacing also includes delivering such pacing stimuli in different ventricles at different times that are separated by an interventricular delay.

In an example of adjusting a cardiac resynchronization therapy in response to the detected edema, such as when biventricular pacing therapy is already being provided, controller 110 adjusts the value of the interventricular delay. In one example, the interventricular delay value is programmable by the user to be approximately between 20 milliseconds and 200 milliseconds, such as about 100 milliseconds. In response to the detected edema, controller 110 incrementally adjusts, over a suitable period of time for allowing the edema to abate, the interventricular delay value to a shorter or longer value until the edema abates or all possible interventricular delay values have been exhausted.

In another example of adjusting a cardiac resynchronization therapy in response to the detected edema, such as when multiple electrodes are associated with a single heart chamber, is to select a different one of the same-chamber electrodes for providing the pacing stimulations associated with that heart chamber. One such possible electrode configuration includes two coronary sinus and/or great cardiac vein electrodes associated with the different locations of the left ventricle. In this example, the left ventricular electrodes are positioned for association with different locations in the left ventricle. For example, such left ventricular electrodes may be positioned in apical, midregion, and basal left ventricular locations. In this example, when left ventricular pacing therapy is being delivered from one of the left ventricular electrodes (with or without corresponding right ventricular pacing therapy), controller 110 responds to the detected edema by shifting to a different left ventricular electrode for providing pacing therapy. In a further example, when left ventricular pacing therapy is being delivered at more than one left ventricular electrode, controller 110 responds to an edema detection by adjusting an interelectrode delay between delivery of the pacing pulses at the different left ventricular electrodes. In one example, the interelectrode delay between delivery of the pacing pulses at the left ventricular electrodes is programmable by the user to values ranging approximately between −100 milliseconds and +100 milliseconds, such as about zero milliseconds. In response to the detected edema, controller 110 incrementally adjusts, over a suitable period of time for allowing the edema to abate, the interelectrode delay value to a shorter or longer value until the edema abates or all possible interelectrode delay values (or, for more than two same-chamber electrodes, all possible combinations of interelectrode delay values) have been exhausted.

In another example, controller 110 responds to an edema detection by initiating or adjusting cardiac contractility modulation (CCM) therapy, such as by using an excitable tissue controller (ETC). CCM therapy includes delivering electrical energy to a portion of the heart during a refractory time period when that portion of the heart is relatively unlikely to contract in response to the received electrical energy. Therefore, CCM therapy need not adjust cardiac rate and, moreover, need not even evoke responsive heart contractions. The electrical energy delivered during the CCM therapy causes an increase in myocardial contractility of the heart muscle, presumably by increasing intracellular calcium concentration. The CCM increase in contractility in turn increases the stroke volume of the heart contractions, so that more blood is pumped by a subsequent systolic contraction. This counteracts and assists in abating the detected edema. Examples of refractory time periods suitable for initiating delivery of CCM therapy include, by way of example, but not by way of limitation, a time period that is approximately between 1 millisecond and 70 milliseconds following an activation (the CCM energy pulse may, in some examples, extend beyond this refractory time period during which the CCM energy pulse is initiated). In one example, the CCM therapy includes electrical energy pulses, each such pulse having an energy that is, by way of example, but not by way of limitation, approximately between 50 microJoules and 500 microJoules. In one example, the CCM energy pulses are delivered as current pulses, each current pulse having an amplitude that is, by way of example, but not by way of limitation, approximately between 0.5 milliamperes and 20 milliamperes, and each current pulse having a pulsewidth that is, by way of example, but not by way of limitation, approximately between 10 milliseconds and 140 milliseconds. In one example, controller 110 responds to an edema detection by initiating CCM therapy delivered, by way of example, but not by way of limitation, from electrode(s) associated with one or both ventricular heart chambers.

In another example, controller 110 responds to the edema detection by adjusting a parameter associated CCM therapy already being delivered, such as by incrementally increasing the energy (e.g., amplitude and/or pulsewidth) from its programmed value to a higher value until the edema abates or all available increased energy levels have been exhausted.

Figure 8:
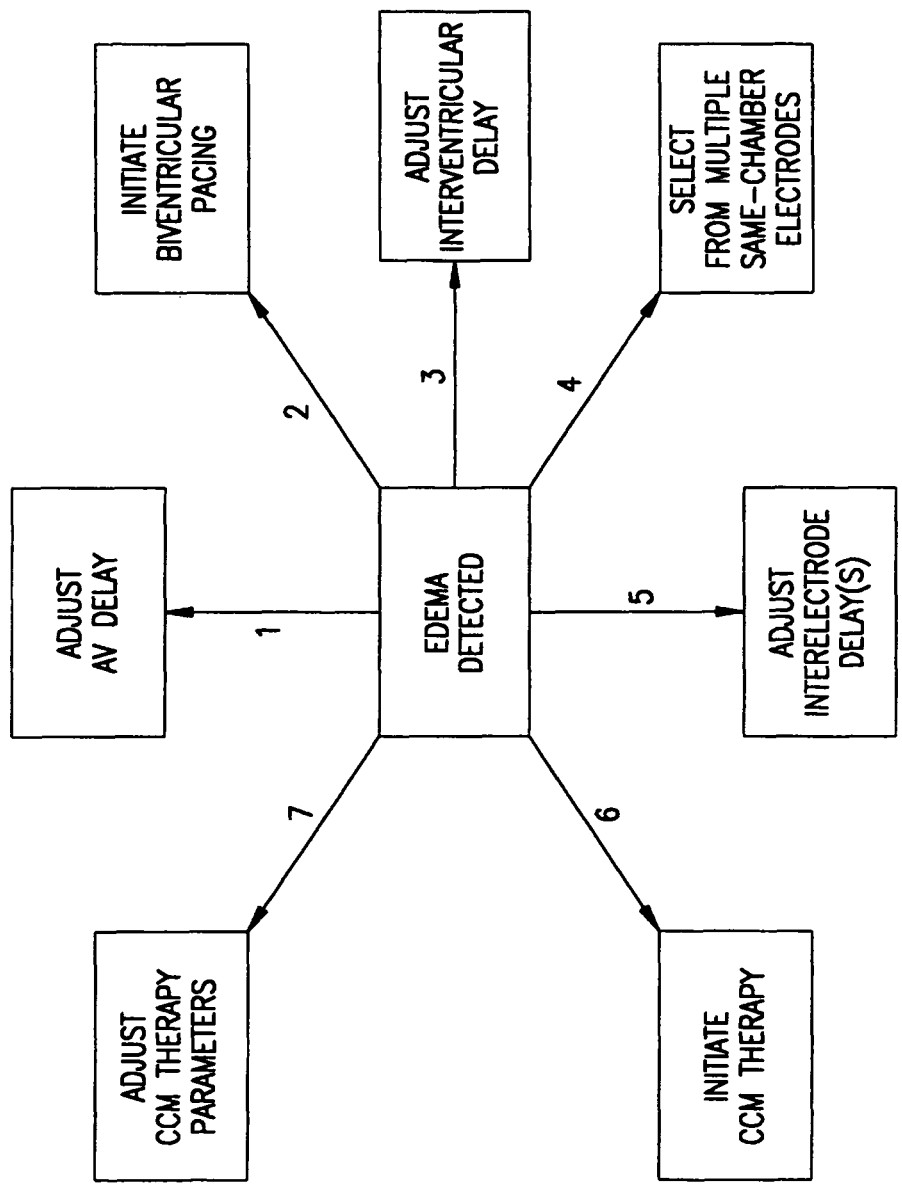
FIG. 8 is a block diagram example in which various responses to a detected edema episode are prioritized.

FIG. 8 is a block diagram example in which various responses to a detected edema episode are prioritized. In this example, controller 110 sequentially attempts the various edema-response measures in the order of priority until the edema abates or all possible responses have been exhausted.

It is to be understood that the above description is intended to be illustrative, and not restrictive. For example, the above-discussed embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. An implantable medical device, comprising:
    edema detection circuitry configured to sense a condition correlative to edema associated with cardiac dysfunction in a subject; and
    therapy delivery circuitry configured to deliver a cardiac therapy in response to said detection, wherein said therapy delivery circuitry provides non-excitatory electrical energy to the heart during a refractory period for the purpose of cardiac contractility modulation.

2. The device of claim 1, wherein the edema detection circuitry comprises an impedance measurement circuit including:
    an exciter configured to provide a high frequency test stimulus to the subject's thorax, the test stimulus being of a type that does not stimulate tissue or muscle contractions in the thorax;
    a preamplifier configured to receive a thoracic signal responsive to the high frequency test stimulus, and to provide a preamplifier output as a function thereof; and
    a demodulator configured to demodulate the preamplifier output.

3. An implantable medical device according to claim 1, wherein the edema detection circuit further comprises:
    a plurality of electrodes configured to be electrically coupled to a patient's heart;
    an impedance measurement circuit coupled to at least one of the electrodes and configured to measure transthoracic impedance; and
    a processor configured to generate a first and a second transthoracic impedance signal based on the measured transthoracic impedance.

4. The device of claim 3, wherein the first transthoracic impedance signal is long-term relative to the second transthoracic impedance signal and wherein the processor is further configured to provide an output based on a difference between the first and second transthoracic impedance signals.

5. The device of claim 4, wherein the processor is further configured to compare the output to a threshold value.

6. The device of claim 5, wherein the processor is further configured to provide an indicator based on the comparison, the indicator relating to fluid buildup in the patient's thorax.

7. The device of claim 3, wherein the processor generates the first and second transthoracic impedance signals based on averaging the measured transthoracic impedance.

8. An implantable medical device according to claim 3, wherein the processor generates the first and second transthoraric impedance signal responsive to a cardiac stroke of said heart.

9. An implantable medical device according to claim 3, wherein the therapy delivery circuit is configured to modify one or more of a timing parameter, a pulse width parameter and a magnitude parameter of the delivery of cardiac therapy based on the first and second transthoracic impedance signals.

10. The device of claim 1, further comprising:
a cardiac pacing circuit coupled to a plurality of electrodes and configured to deliver pacing therapy to the patient's heart.

11. The device of claim 10, wherein the pacing therapy includes cardiac resynchronization therapy.

12. The device of claim 1, further comprising: a housing adapted for implantation in the patient; wherein the impedance measurement circuit and the processor are disposed in the housing.

13. The device of claim 12, further comprising:
a cardiac pacing circuit coupled to at least some of the plurality of electrodes and configured to deliver pacing therapy to the patient's heart;
wherein the cardiac pacing circuit is also disposed in the housing.

14. A device adapted to be implanted in a patient, comprising:
an implantable cardiac rhythm management apparatus including a circuit housing and a plurality of electrodes;
a cardiac pacing circuit disposed in the housing and coupled to at least some of the electrodes to deliver pacing therapy to the patient's heart;
an impedance measurement circuit disposed in the housing, coupled to at least some of the electrodes, and configured to measure a transthoracic impedance of the patient, the impedance measurement circuit including (a) an exciter circuit configured to apply a high frequency test stimulus to the patient's thorax, the test stimulus being of a type that does not stimulate tissue or muscle contractions in the thorax, (b) a preamplifier configured to receive a transthoracic response signal associated with the high frequency test stimulus, and configured to provide a preamplifier output as a function thereof, and (c) a demodulator configured to demodulate the preamplifier output;
a processor disposed in the housing and being configured to (a) receive the measured transthoracic impedance from the impedance measurement circuit, (b) generate first and second transthoracic impedance signals by averaging the measured transthoracic impedance, the first transthoracic impedance signal being long-term relative to the second transthoracic impedance signal, (c) compare the first and second thoracic impedance signals, and (d) provide an indicator based on the comparison, the indicator relating to fluid buildup in the patient's thorax and taking into account a cardiac stroke of said heart; and
therapy delivery circuitry configured to modify one or more of a timing parameter, a pulse width parameter and a magnitude parameter of the delivery of cardiac therapy based on the indicator, wherein said cardiac therapy includes the therapeutic delivery of non-excitatory electrical energy to the heart during a refractory period for the purpose of cardiac contractility modulation.

15. The device of claim 14, wherein the first transthoracic impedance signal is a long-term value of the second transthoracic impedance signal.

16. The device of claim 14, wherein the first transthoracic impedance signal is characterized by a delay relative to the second transthoracic impedance signal.

17. The device of claim 14, wherein the processor generates a difference signal from the comparison of the first and second thoracic impedance signals.

18. The device of claim 17, wherein the processor provides the indicator as a function of the difference signal and a threshold value.

19. A method of monitoring fluid buildup and providing corrective therapy to a patient, comprising:
measuring a transthoracic impedance of the patient;
determining edema associated with a cardiac dysfunction based on the measured transthoracic impedance; and
delivering a corrective cardiac therapy signal based on the determination, wherein said cardiac therapy includes the therapeutic delivery of non-excitatory electrical energy to the heart during a refractory period for the purpose of cardiac contractility modulation.

20. A method according to claim 19, further comprising:
providing a plurality of electrodes for implantation in the patient;
delivering cardiac pacing therapy to the patient's heart using at least some of the electrodes,
wherein said measuring further comprises (a) applying a high frequency test stimulus to the patient's thorax using at least some of the electrodes, the test stimulus being of a type that does not stimulate tissue or muscle contractions in the thorax, (b) receiving a transthoracic response signal associated with the high frequency test stimulus, and (c) demodulating the response signal;
generating first and second transthoracic impedance signals by averaging the measured transthoracic impedance, the first transthoracic impedance signal being long-term relative to the second transthoracic impedance signal;
comparing the first and second thoracic impedance signals; and
providing an indicator based on the comparison, the indicator relating to fluid buildup in the patient's thorax.

21. The method of claim 20, wherein the the first transthoracic impedance signal is a long-term value of the second transthoracic impedance signal.

22. The method of claim 20, wherein the the first transthoracic impedance signal is delayed relative to the second transthoracic impedance signal.

23. The method of claim 20, wherein the first and second thoracic impedance signals are compared by generating a difference signal from the two thoracic impedance signals.

24. The method of claim 23, wherein the indicator provided is a function of the difference signal and a threshold value.

25. A method according to claim 20, wherein the indicator is responsive to a cardiac stroke of said heart.

26. A method according to claim 20, wherein one or more of a timing parameter, a pulse width parameter and a magnitude parameter of the corrective therapy signal is modified in response to said indicator.

* * * * *